US012594137B2

(12) United States Patent
Hourtash et al.

(10) Patent No.: US 12,594,137 B2
(45) Date of Patent: Apr. 7, 2026

(54) HARD STOP PROTECTION SYSTEM AND METHOD

(71) Applicant: Intuitive Surgical Operations, Inc., Sunnyvale, CA (US)

(72) Inventors: Arjang Hourtash, Sunnyvale, CA (US); Goran Lynch, Sunnyvale, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 0 days.

(21) Appl. No.: 18/649,939

(22) Filed: Apr. 29, 2024

(65) Prior Publication Data

US 2024/0350219 A1      Oct. 24, 2024

Related U.S. Application Data

(63) Continuation of application No. 17/264,384, filed as application No. PCT/US2019/044123 on Jul. 30, 2019, now Pat. No. 11,998,296.

(Continued)

(51) Int. Cl.
*A61B 34/00*       (2016.01)
*A61B 34/30*       (2016.01)
(Continued)

(52) U.S. Cl.
CPC .............. *A61B 34/77* (2016.02); *A61B 34/35* (2016.02); *A61B 34/37* (2016.02); *A61B 34/74* (2016.02);
(Continued)

(58) Field of Classification Search
CPC ......... A61B 34/77; A61B 34/35; A61B 34/37; A61B 34/74; A61B 34/76; A61B 34/70;
(Continued)

(56) References Cited

U.S. PATENT DOCUMENTS 4,184,688 A *   1/1980   Omura ................. G11B 3/0857
6,645,196 B1    11/2003   Nixon et al.
(Continued)

FOREIGN PATENT DOCUMENTS

WO     WO-2016149308 A1 *  9/2016  ............ B25J 13/025
WO     WO-2017127202 A1   7/2017
WO     WO-2017160458 A1   9/2017

OTHER PUBLICATIONS

International Preliminary Report on Patentability for Application No. PCT/2019/044123, mailed on Feb. 11, 2021, 14 pages.
(Continued)

*Primary Examiner* — Adam R Mott
*Assistant Examiner* — Byron Xavier Kasper
(74) *Attorney, Agent, or Firm* — Osha Bergman Watanabe & Burton LLP

(57)       ABSTRACT

Disclosed herein are apparatus and method for resisting external articulation of one or more joints of a manipulator assembly when the joints are approaching mechanical limits. For example, an articulable system may include a joint mechanism, an actuator coupled to the joint mechanism, a sensor system for sensing a joint state and a controller. The controller can operate the articulable system in an external articulation facilitation mode. The controller can command the actuator to resist movement of the joint in response to the joint state indicating the joint is moving toward a mechanical limit location with a joint velocity meeting a first velocity criterion. The controller can also command the actuator resist movement of the joint at a second joint position when the joint velocity meets a second criterion.

20 Claims, 7 Drawing Sheets

Related U.S. Application Data

(60) Provisional application No. 62/712,784, filed on Jul. 31, 2018, provisional application No. 62/711,990, filed on Jul. 30, 2018.

(51) Int. Cl.

| | | |
|---|---|---|
| *A61B 34/35* | (2016.01) | |
| *A61B 34/37* | (2016.01) | |
| *B25J 9/00* | (2006.01) | |
| *B25J 9/16* | (2006.01) | |

(52) U.S. Cl.

CPC ............. *A61B 34/76* (2016.02); *B25J 9/0045* (2013.01); *B25J 9/1676* (2013.01); *B25J 9/1689* (2013.01)

(58) Field of Classification Search

CPC ......... A61B 34/30; A61B 34/10; A61B 34/00; A61B 34/32; A61B 2090/508; A61B 90/03; B25J 9/0045; B25J 9/1676; B25J 9/1689; B25J 9/00; B25J 9/16; B25J 9/02; B25J 9/023; B25J 9/1005; B25J 9/101; B25J 9/12; B25J 9/123; B25J 9/161; B25J 9/1651; B25J 9/1656; B25J 9/1664; B25J 9/1674; B25J 9/1692; B25J 13/088; B25J 19/0004; B25J 19/0091; B25J 19/06; G05B 2219/40195; G05B 2219/40598; G05B 19/416; A63B 23/129

See application file for complete search history.

(56) References Cited

U.S. PATENT DOCUMENTS

| | | | |
|---|---|---|---|
| 9,592,608 | B1 | 3/2017 | Bingham et al. |
| 11,998,296 | B2 | 6/2024 | Hourtash et al. |

| | | | | |
|---|---|---|---|---|
| 2003/0029463 | A1* | 2/2003 | Niemeyer | ........... H04N 13/239 |
| | | | | 348/E13.016 |
| 2007/0142825 | A1 | 6/2007 | Prisco et al. | |
| 2008/0207289 | A1 | 8/2008 | Kang | |
| 2008/0309273 | A1* | 12/2008 | Kamiya | ............... B25J 19/0004 |
| | | | | 318/563 |
| 2012/0109374 | A1* | 5/2012 | Lee | ...................... G05B 19/416 |
| | | | | 700/245 |
| 2012/0224464 | A1* | 9/2012 | Kim | ................... G11B 7/08511 |
| 2014/0297030 | A1* | 10/2014 | Iwasaki | ................ G05B 19/416 |
| | | | | 700/245 |
| 2016/0030118 | A1 | 2/2016 | Devengenzo et al. | |
| 2016/0030119 | A1 | 2/2016 | Devengenzo et al. | |
| 2017/0007336 | A1 | 1/2017 | Tsuboi et al. | |
| 2017/0071680 | A1 | 3/2017 | Swarup et al. | |
| 2017/0112580 | A1* | 4/2017 | Griffiths | ............... F16M 13/022 |
| 2017/0136624 | A1 | 5/2017 | Hourtash et al. | |
| 2017/0197312 | A1 | 7/2017 | Osada et al. | |
| 2018/0049829 | A1* | 2/2018 | Yates | .................... A61B 34/30 |
| 2018/0250004 | A1 | 9/2018 | Williams et al. | |
| 2018/0297204 | A1 | 10/2018 | Krasny et al. | |
| 2020/0197108 | A1 | 6/2020 | Usui | |
| 2022/0110705 | A1 | 4/2022 | Hourtash et al. | |

OTHER PUBLICATIONS

International Search Report and Written Opinion for Application No. PCT/US2019/044123, mailed on Oct. 25, 2019, 20 pages.

Vertut, J., and Coiffet, P., "Robot Technology: Teleoperation and Robotics Evolution and Development," English translation, Prentice-Hall, Inc., Inglewood Cliffs, NJ, USA 1986, vol. 3A, 332 pages.

\* cited by examiner

*500*

FACILITATE EXTERNAL ARTICULATION
502

DETERMINE JOINT STATE (VELOCITY, POSITION, DIRECTION)
503

DETERMINE JOINT VELOCITY THRESHOLD
504

VELOCITY THRESHOLD EXCEEDED?
506

NO

YES

DETERMINE MAGNITUDE EXCEEDED
508

CALCULATE RESISTANCE
510

INSTRUCT ACTUATOR TO APPLY RESISTANCE
512

HARD STOP PROTECTION SYSTEM AND METHOD

CROSS REFERENCE TO RELATED APPLICATIONS

This application is a continuation of and claims the benefit of priority under 35 U.S.C. § 120 to U.S. patent application Ser. No. 17/264,384, filed Jan. 29, 2021, which is a national stage application filed under 35 U.S.C. § 371 of PCT/US2019/044123, filed Jul. 30, 2019, which claims the benefit of U.S. Provisional Patent Application Ser. No. 62/711,990 filed Jul. 30, 2018, and U.S. Provisional Patent Application Ser. No. 62/712,784 filed Jul. 31, 2018, the disclosures of which are expressly incorporated herein by reference.

TECHNICAL FIELD

The present disclosure is directed to manipulator systems and in particular control of joint mechanisms in manipulator systems.

BACKGROUND

A robotic system can be used to perform a task at a worksite. For example, robotic systems can include robotic manipulators to manipulate instruments for performing tasks at the worksite.

Examples of robotic systems include industrial and recreational robotic systems. Examples of robotic systems also include medical robotic systems used in procedures for diagnosis, non-surgical treatment, surgical treatment, etc. As a specific example, robotic systems include minimally invasive, robotic telesurgical systems in which a surgeon can operate surgically on a patient from bedside or a remote location. Telesurgery refers generally to surgery performed using surgical systems where the surgeon uses some form of remote control, e.g., a servomechanism, to manipulate surgical instrument movements rather than directly holding and moving the instruments by hand. A robotic medical system usable for telesurgery or other telemedical procedures can include one or more remotely controllable robotic manipulators. Operators can remotely control motion of the remotely controllable robotic manipulator(s). Operators can also manually articulate or otherwise move portions of the robotic medical system into positions or orientations within the surgical environment.

A robotic manipulator can include two or more links coupled together by one or more joint mechanisms. In some instances, a joint mechanism has one or more mechanical limits—sometimes called hard stops—to the range of motion of the joint mechanism; in this way, the mechanical limits limit the joints provided by the joint mechanisms, and the relative motion of the links connected to the joint mechanisms. A revolute joint mechanism, for instance, operate to provide a single rotational degree-of-freedom; this rotational degree-of-freedom may be limited to no more than maximum angle at which physical components of the joint mechanism provides a mechanical limit or "hard stop" that limits, by hindering or completely stopping, further rotation beyond the maximum angle. Also, a revolute joint mechanism may have a minimum angle at which physical components of the joint mechanism provides a minimum-angle mechanical limit or "hard stop" that limits further rotation below the minimum angle. Similarly, a prismatic joint mechanism may have one or more mechanical limits that impose one or more limits (such as maximum or minimum limits), on the linear displacement of the prismatic joint mechanism. Impact against a mechanical limit, or other applications of force urging joint mechanism motion past the mechanical limit provided by the mechanical limit may cause vibrations, errant motion, or overload the joint mechanism and cause damage. It would be advantageous to reduce, bound, control, or avoid such vibrations, errant motions, or overloading of joint mechanism mechanical limits.

SUMMARY OF THE INVENTION

Disclosed herein are control systems for resisting external articulation of joint mechanisms of manipulator assemblies when approaching mechanical limits of the joint mechanisms. For example, a control system can, when operating in a mode assisting externally directed articulation of the manipulator assembly, determine when a threshold velocity has been exceeded and instruct an actuator to resist movements of a joint above the threshold velocity. As another example, the control system can also instruct the actuator to apply increasing amounts of resistance in proportion to an amount the actual velocity of the joint exceeds the threshold velocity to dissipate kinetic energy. As a further example, the control system can apply a decreasing threshold velocity as the joint moves within a transitional position and closer to a mechanical limit location of a mechanical limit of the joint mechanism. As yet another example, the control system can allow joint velocities that fall below a minimum threshold velocity without applying resistance regardless of how close the joint is to the mechanical limit location.

In one embodiment, an articulable system includes a joint mechanism, an actuator, a sensor and a controller. The joint mechanism implements a joint and has a mechanical limit. The mechanical limit defines a mechanical limit location. The actuator is physically coupled to the joint mechanism. The sensor system is associated with the joint mechanism and is configured to sense a joint state of the joint. The controller is connected for communication with the sensor system and the actuator. The controller includes a memory storing a plurality of velocity criteria. A first velocity criterion of the plurality of velocity criteria is associated with the joint being at a first joint position and moving toward the mechanical limit location. The second joint velocity criterion of the plurality of velocity criteria is associated with the joint being at a second joint position and moving toward the mechanical limit location. The controller is configured to operate the articulable system in a first mode. In the first mode, the controller operates the actuator to facilitate external articulation of the joint mechanism, commands the actuator to resist movement of the joint in response to the joint state indicating the joint at the first joint position and moving toward the mechanical limit location with a joint velocity meeting the first velocity criterion, and commands the actuator to resist movement of the joint in response to the joint state indicating the joint at the second joint position and moving toward the mechanical limit location with a joint velocity meeting the second velocity criterion. The joint state may comprise a joint position and a joint velocity, for example.

In another embodiment, the first joint position is farther from the mechanical limit location than the second joint position. And the first velocity criterion comprises a first speed threshold and the second velocity criterion comprises a second speed threshold. The second speed threshold is lower than the first speed threshold.

In another embodiment, the controller commands the actuator, in response to the joint state indicating the joint at the second joint position and moving toward the mechanical limit location with the joint velocity meeting the second velocity criterion, to resist movement of the joint with a first resistance. And the controller is further configured to, in the first mode, not command the actuator to resist movement of the joint with the first resistance in response to the joint state indicating the joint being at the second joint position and moving away from the mechanical limit location with the joint velocity meeting the second velocity criterion.

In another embodiment, the plurality of velocity criteria further comprises a third velocity criterion associated with the joint being at the second joint position and moving away from the mechanical limit location. Also, the third velocity criterion comprises a third speed threshold higher than a second speed threshold of the second velocity criterion. And the controller is further configured to, in the first mode, command the actuator to resist movement of the joint in response to the sensor system sensing the joint being at the second joint position and moving away from the mechanical limit location with a speed exceeding the third speed threshold.

In another embodiment, the plurality of velocity criteria further comprises a fourth velocity criterion associated with the joint being at the first joint position and moving away from the mechanical limit location. The fourth velocity criterion comprises a fourth speed threshold equal to the third speed threshold. And the controller is further configured to, in the first mode, command the actuator to resist movement of the joint in response to the sensor system sensing the joint being at the first joint position and moving away from the mechanical limit location with a speed exceeding the fourth speed threshold.

In another embodiment, the controller is further configured to operate the articulable system in a second mode. For example, in the second mode, the controller operates the actuator not to facilitate the external articulation of the joint.

In another embodiment, the articulable system further includes a user input device. For example, the user input device is configured to accept a movement command to teleoperatively move the joint. And the controller is further configured to, in the second mode, operate the actuator to move the joint in response to the movement command.

In another embodiment, the articulable system is a robotic system comprising a manipulator arm, the manipulator arm comprising the actuator, the sensor system, and a kinematic series comprising the joint mechanism.

In another embodiment, the robotic system is a medical robotic system. The manipulator arm further comprises a tool interface configured to releasably support a medical tool. And the medical robotic system further includes a user input device configured to accept a movement command to move the medical tool, wherein the controller is further configured to, in the second mode and in response to the movement command, command movement of the manipulator arm to move the medical tool.

In another embodiment, the sensor system comprises: a velocity sensor configured to sense a velocity of the joint or a position sensor configured to sense a position of the joint.

In another embodiment, the plurality of velocity criteria comprises a velocity profile associating each velocity criterion of the plurality of velocity criteria with at least one joint position.

In another embodiment, the plurality of velocity criteria comprises the velocity profile by including an equation yielding velocity criterion as a function of joint position.

In another embodiment, the velocity profile has a constant velocity criteria portion and the first velocity criterion is within the constant velocity criteria portion.

In another embodiment, the velocity profile has a decreasing velocity criteria portion and the second velocity criterion is within the decreasing velocity criteria portion.

In another embodiment, the decreasing velocity criteria portion has velocity criteria decreasing as a distance the joint is from the mechanical limit location decreases.

In another embodiment, the decreasing velocity criteria portion has velocity criteria linearly proportionately lower relative to the distance the joint is from the mechanical limit location.

In another embodiment, the plurality of velocity criteria include a minimum velocity criterion associated with the joint being at the mechanical limit location, and the minimum velocity criterion comprises a speed threshold greater than zero.

In another embodiment, in the first mode, the controller is configured to instruct the actuator to resist movement of the joint from the first joint position with a resistance magnitude based on an amount the joint velocity exceeds the first velocity criterion.

In another embodiment, the resistance magnitude is in proportion to the amount the joint velocity exceeds the first velocity criterion.

In another embodiment, the actuator includes a brake configured to resist movement of the joint. For example, the brake may be a multi-level, electromagnetic brake.

In another embodiment, the joint mechanism is a single degree-of-freedom rotatable joint coupling two links.

In another embodiment, the actuator resisting movement of the joint dissipates a kinetic energy of the movement of the joint.

In another embodiment, the mechanical limit is a first mechanical limit and wherein the joint mechanism includes a second mechanical limit defining a second mechanical limit location. A third velocity criterion of the plurality of velocity criteria is associated with the joint being at a third joint position and moving toward the second mechanical limit location. A fourth velocity criterion is associated with the joint being at a fourth joint position and moving toward the second mechanical limit location. And, in the first mode, the controller further commands the actuator to resist movement of the joint in response to the joint state indicating the joint at the third joint position and moving toward the second mechanical limit with a joint velocity meeting the third velocity criterion. And the controller further commands the actuator to resist movement of the joint in response to the joint state indicating the joint at the fourth joint position and moving toward the second mechanical limit with a joint velocity meeting the fourth velocity criterion.

In another embodiment, the first and second mechanical limits locations are on opposite ends of motion of the joint mechanism.

Other embodiments include a method of operating an articulable system. The articulable system includes a joint mechanism implementing a joint, an actuator physically coupled to the joint mechanism, a sensor system associated with the joint mechanism, and a controller. The joint mechanism comprises a mechanical limit defining a mechanical limit location. The method includes accessing, with the controller, a plurality of velocity criteria, wherein a first velocity criterion of the plurality of velocity criteria is associated with the joint being at a first joint position and moving toward the mechanical limit location, and a second velocity criterion is associated with the joint being at a second joint position and moving toward the mechanical limit location. And, while the articulable system is operating in a first mode, operating the actuator to facilitate external articulation of the joint. Further, determining a joint state using information from the sensor system, wherein the joint state comprises a joint position and a joint velocity. Also, commanding the actuator to resist movement of the joint in response to the joint state indicating the joint at the first joint position and moving toward the mechanical limit location with a joint velocity meeting the first velocity criterion. And commanding the actuator to resist movement of the joint in response to the joint state indicating the joint at the second joint position and moving toward the mechanical limit location with a joint velocity meeting the second velocity criterion. The method also includes, while the articulable system is operating in a second mode, operating the actuator not to facilitate external articulation of the joint.

The method may also include the joint position being is farther from the mechanical limit location than the second joint position. And the first velocity criterion comprising a first speed threshold and the second velocity criterion comprises a second speed threshold lower than the first speed threshold.

In another embodiment, the method includes resisting with a first resistance as part of commanding the actuator to resist movement of the joint in response to the joint state indicating the joint at the second joint position and moving toward the mechanical limit location with a joint velocity meeting the second velocity criterion. And, while the articulable system is operating in the first mode, not commanding the actuator to resist movement of the joint with the first resistance in response to the joint state indicating the joint being at the second joint position and moving away from the mechanical limit location with the joint velocity meeting the second velocity criterion.

In another embodiment, the plurality of velocity criteria further comprises a third velocity criterion associated with the joint being at the second joint position and moving away from the mechanical limit location. Also, the third velocity criterion comprises a third speed threshold higher than a second speed threshold of the second velocity criterion. The method further includes, while the articulable system is operating in the first mode, commanding the actuator to resist movement of the joint in response to the sensor system sensing the joint being at the second joint position and moving away from the mechanical limit location with a speed exceeding the third speed threshold.

In another embodiment, the plurality of velocity criteria further comprises a fourth velocity criterion associated with the joint being at the first joint position and moving away from the mechanical limit location. Also, the fourth velocity criterion comprises a fourth speed threshold equal to the third speed threshold. The method further includes while the articulable system is operating in the first mode, commanding the actuator to resist movement of the joint in response to the sensor system sensing the joint being at the first joint position and moving away from the mechanical limit location with a speed exceeding the fourth speed threshold.

Another embodiment includes, while the articulable system is operating in the second mode, operating the actuator to move the joint in response to a movement command to teleoperatively move the joint, the movement command received at a user input device configured to accept the movement command.

In another embodiment, the articulable system is a robotic system comprising a user input device configured to accept a movement command to move a tool, and a manipulator arm. The manipulator arm comprises the actuator, the sensor system, a kinematic series comprising the joint mechanism, and a tool interface configured to releasably support the tool. The method includes, while the articulable system is operating in the second mode, commanding movement of the manipulator arm to move the tool in response to the movement command.

In another embodiment, the plurality of velocity criteria comprises a velocity profile associating each velocity criterion of the plurality of velocity criteria with at least one joint position.

In another embodiment, the velocity profile has a constant velocity criteria portion and the first velocity criterion is within the constant velocity criteria portion. And the velocity profile has a decreasing velocity criteria portion and the second velocity criterion is within the decreasing velocity criteria portion. Further the decreasing velocity criteria portion has velocity criteria decreasing as a distance the joint is from the mechanical limit location decreases. And the decreasing velocity criteria portion has velocity criteria linearly proportionately lower relative to the distance the joint is from the mechanical limit location.

In another embodiment, the plurality of velocity criteria include a minimum velocity criterion associated with the joint being at the mechanical limit location. And the minimum velocity criterion comprises a speed threshold greater than zero.

In another embodiment, commanding the actuator to resist movement of the joint in response to the joint state indicating the joint at the first joint position and moving toward the mechanical limit location with a joint velocity meeting the first velocity criterion further includes instructing the actuator to resist movement of the joint from the first joint position with a resistance magnitude based on an amount the joint velocity exceeds the first velocity criterion.

In another embodiment, the resistance magnitude is in proportion to the amount the joint velocity exceeds the first velocity criterion.

In another embodiment, commanding the actuator to resist movement of the joint in response to the joint state indicating the joint at the first joint position and moving toward the mechanical limit location with a joint velocity meeting the first velocity criterion further includes causing dissipation of a kinetic energy of the movement of the joint.

Another embodiment includes non-transitory machine-readable medium comprising a plurality of machine-readable instructions which when executed by one or more processors associated with an articulable system comprising a joint mechanism having a mechanical limit location defined by a mechanical limit, an actuator physically coupled to the joint mechanism, a sensor system associated with the joint mechanism, and a controller, are adapted to cause the one or more processors to perform the method described herein.

Embodiments of the present invention can provide many advantages. For example, the systems and methods disclosed herein can help to protect against overriding a mechanical limit, especially in a manipulator assembly employing high mass links. In addition, because the system generates a resistance, it can be used for externally (outside of the controllers) applied articulations when restricting articulation commands from the control system may not arrive in time or be proportioned enough to avoid impacts. Also, the systems and methods allow for increased amounts of dissipation of kinetic energy sooner when a joint is closer to its mechanical limits. At the same time, the systems and methods can allow for un-resisted movement in the proximity of the mechanical limits below a certain threshold. Further, embodiments may be used in conjunction with other protective control schemes, including those in modes where external articulations are being applied to the joint.

BRIEF DESCRIPTIONS OF THE DRAWINGS

DETAILED DESCRIPTION

In the following description, specific details are set forth describing some embodiments consistent with the present disclosure. Numerous specific details are set forth in order to provide a thorough understanding of the embodiments. It will be apparent, however, to one skilled in the art that some embodiments may be practiced without some or all of these specific details. The specific embodiments disclosed herein are meant to be illustrative but not limiting. One skilled in the art may realize other elements that, although not specifically described here, are within the scope and the spirit of this disclosure. In addition, to avoid unnecessary repetition, one or more features shown and described in association with one embodiment may be incorporated into other embodiments unless specifically described otherwise or if the one or more features would make an embodiment non-functional.

For example, although some of the embodiments described herein refer to surgical procedures or tools, or medical procedures and medical tools, the techniques disclosed apply to medical and non-medical procedures, and to medical and non-medical tools. For example, the tools, systems, and methods of any of the embodiments described herein may be used for non-medical purposes including industrial uses, general robotic uses, and sensing or manipulating non-tissue work pieces. Other example applications involve cosmetic improvements, imaging of human or animal anatomy, gathering data from human or animal anatomy, setting up or taking down the system, and training medical or non-medical personnel. Additional example applications include use for procedures on tissue removed from human or animal anatomies (without return to a human or animal anatomy), and performing procedures on human or animal cadavers. Further, these techniques can also be used for medical treatment or diagnosis procedures that do, or do not, include surgical aspects.

In some instances well known methods, procedures, components, and circuits have not been described in detail so as not to unnecessarily obscure aspects of the embodiments.

Figure 1:
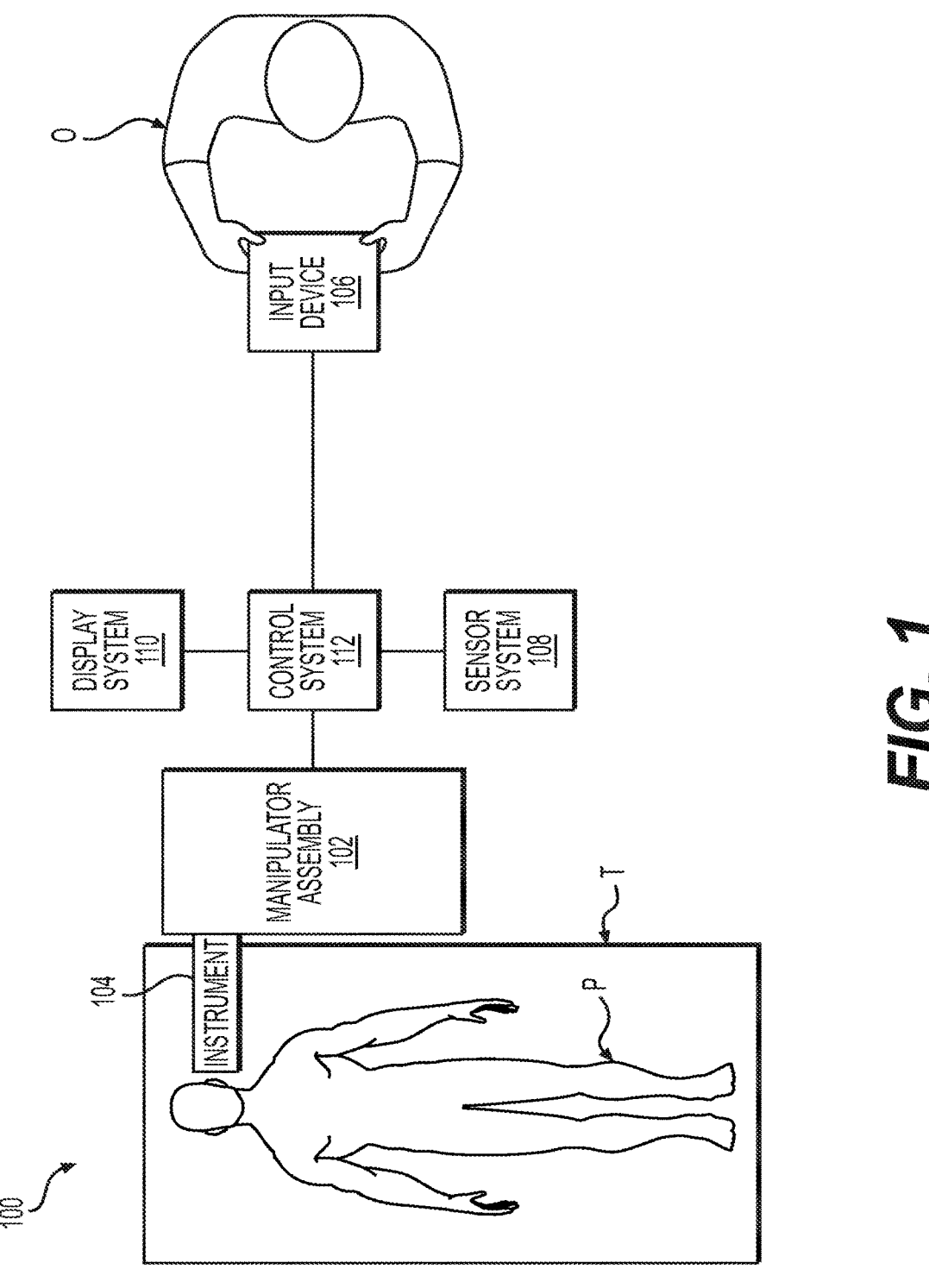
FIG. 1 is a simplified diagram of a teleoperated medical system according to some embodiments of the present invention.

FIG. 1 is a general, simplified diagram of a robotic system. Aspects of the robotic system shown in FIG. 1 can be selectively used alone and in combination with other embodiments described herein, although not by way of limiting those embodiments. Specifically, FIG. 1 shows a teleoperated medical system 100 according to some embodiments. In some embodiments, teleoperated medical system 100 may be suitable for use in, for example, surgical, diagnostic, therapeutic, or biopsy procedures. Teleoperated medical system 100 may, for example, include a da Vinci® Surgical System commercialized by Intuitive Surgical, Inc. As noted above, while some embodiments are provided herein with respect to such procedures, any reference to medical or surgical instruments and medical or surgical methods is non-limiting. The systems, instruments, and methods of any of the embodiments shown or described herein may be used, for example, for animals, human cadavers, animal cadavers, portions of human or animal anatomy, non-surgical diagnosis, as well as for industrial systems and general robotic or teleoperational systems.

As shown in FIG. 1, medical system 100 generally includes a manipulator assembly 102 for operating a medical instrument 104 in performing various procedures on a patient P. The manipulator assembly 102 may be teleoperated, non-teleoperated, combined teleoperated and non-teleoperated. Examples of combined teleoperated and non-teleoperated use of a manipulator assembly 102 include: a same manipulator assembly portion being controlled by a command that combine teleoperated and non-teleoperated inputs, a same manipulator assembly portion being teleoperated and non-teleoperated at different times, or a first portion of the manipulator assembly 102 being teleoperated and a second portion of the manipulator assembly 102 being non-teleoperated (such as with a first set of degrees of freedom of motion that is teleoperated and a second set of degrees of freedom of motion that is non-teleoperated). During use, manipulator assembly 102 is located near a patient P, such as parked, braked, or mounted to or near an operating table T. An input device 106 allows an operator O (e.g., a surgeon or some other clinician, a nurse, an assistant, or some other medical or non-medical personnel, as illustrated in FIG. 1) to view the interventional site and to control manipulator assembly 102. In some embodiments, the input device 106 may comprise a master assembly where motion of the master assembly is mimicked or mirrored by the instrument 104 or the manipulator assembly 102, such that motion of the master assembly defines the input that controls the motion of the instrument 104 or the manipulator assembly 102.

In the example of FIG. 1, input device 106 is located at an operator console, although other implementations may comprise input devices that are not attached or stationed at any operator consoles. In the example of FIG. 1, the operator console is located in the same room as operating table T, such as at the side of an operating table on which patient P is located. However, it should be understood that the console and operator O can be located in a different room or a completely different building from patient P in various embodiments. Input device 106 generally includes one or more devices for controlling manipulator assembly 102, such as any number of joysticks, trackballs, data gloves, trigger-guns, hand-operated controllers, voice recognition devices, body motion or presence sensors, and/or the like.

Manipulator assembly 102 supports one or more medical instruments 104 (one medical instrument 104 is shown in FIG. 1 for case of explanation). Manipulator assembly 102 includes one or more manipulator arms, where each manipulator arm may include a kinematic structure of a plurality of links and a plurality of joint mechanisms. A joint mechanism can be connected to links, and provide a joint that allows relative motion of the links. For example, a joint mechanism may be a single degree-of-freedom joint mechanism, such as a revolute or prismatic joint mechanism that provides a joint configured for rotary or linear motion. A joint mechanism may also be a multi-degree-of-freedom joint mechanism, such as ball joint mechanisms that provide two degrees of freedom. The configuration of the manipulator arm may then be determined based on the positions and orientations of its joint mechanisms, and the geometry of its links.

A joint mechanism of a manipulator arm of manipulator assembly 102 can be implemented as a driven joint, such that the joint can be articulated using actuators coupled to the joint mechanisms. A joint mechanism can also be implemented as a non-driven joint mechanism that cannot be articulated using actuators coupled to the joint mechanism. For example, a non-driven joint mechanism may be coupled to no actuators, coupled only to actuators that apply resistive and not motive force, or coupled to actuators incapable of providing sufficient motive force to articulate the joint provided ty the joint mechanism. Both driven and non-driven joint mechanisms may be coupled to brakes that can be engaged to resist or stop motion.

One or more of the plurality of joint mechanisms of the manipulator assembly 102, driven or non-driven, may be configured to be manually positioned and locked in place during use. Driven joint mechanisms may be configured to be teleoperated or non-teleoperated during operation. Non-driven joint mechanisms may still include motors, brakes, or other actuators that facilitate manual positioning and locking of the joint mechanisms. The actuators can be operated to facilitate the articulation of the joints or links during set-up or use of the manipulator assembly 102. The plurality of joint mechanisms, for example, may include one or more joint mechanisms that may be actuated in response to commands from the control system to move the joint mechanism without external articulating force, to provide forces that positively assist external articulation of the joint mechanism, to balance against gravity, to reduce braking forces on the joint mechanism, etc. The term "actuator" as used herein should be construed broadly to include actuated drive or brake mechanisms, including motors and brakes, and including actuators driven by electricity, pneumatics, hydraulics, magnetic forces, etc.

Manipulator assembly 102 may also include a plurality of actuators that apply inputs on medical instrument 104 in response to commands from the control system (e.g., a control system 112). The actuators may include drive systems that, when coupled to medical instrument 104, may advance medical instrument 104 into a naturally or surgically created anatomic orifice. Additionally, the actuators can be used to actuate a distal tool of the medical instrument 104, such as move an articulable end effector of a medical instrument 104 for grasping tissue in the jaws of a biopsy device and/or the like.

As will be described more herein, joints of the manipulator assembly 102 and/or the medical instrument 104 may be moved in a first, external articulation facilitation mode via external application of forces to articulate its joints with facilitation by actuators. An example of this first mode is a set-up or reconfiguration mode where personnel move robotic manipulator(s) of the manipulator assembly 102 into position adjacent and above the operating table T. For example, a physician or other personnel may manually grasp a portion of the manipulator assembly 102 and/or medical instrument 104, and pull or push that portion toward a particular position or orientation, such as a position above a patient orifice or aligned toward the patient orifice. In another, second mode, the operator O provides inputs via the input device 106 to drive motion of the manipulator assembly 102 and the medical instrument 104. For example, the operator O can move a portion of the input device 106, and the control system 112 can command actuators of the manipulator assembly 102 to operate such that the medical instrument 104 follows the articulation of the portion of the input device 106.

Medical system 100 may include a sensor system 108 with one or more sub-systems for receiving information about the instruments, joint mechanisms, links, or other components of manipulator assembly 102. Such sub-systems may include a position/location sensor system (e.g., an electromagnetic sensor system); a shape sensor system for determining the position, orientation, speed, velocity, acceleration, pose, and/or shape of a distal end and/or of one or more sections of medical instrument 104 or components of manipulator assembly 102; and/or a visualization or other sensor system for capturing images or other data from the distal end of medical instrument 104. The sensor system 108 may also include actuator or joint position sensors such as resolvers, encoders, potentiometers, and other mechanisms. This position sensor data may be used to determine motion of the joint mechanisms, links and objects manipulated by the actuators. The sensor system 108 may also include, for example, magnetic field sensors such as hall effect sensors that provide position information, velocity sensors such as tachometers, accelerometers, gyroscopes, IMUs (inertial measurement units), magnetometers (such as for orientation). Acceleration data may be integrated over time to provide velocity and/or position information, Velocity data may be integrated over time to provide position information.

The sensor system 108 may use the above or additional mechanisms to report on a joint state of a joint mechanism of the manipulator assembly 102. State information, for example, can include a position and/or some time-based variable, such as velocity or acceleration, of the joint provided by the joint mechanism. The sensor system 108, for example, may include an encoder or potentiometer that reports on an angle for a single degree-of-freedom rotary joint provided by a revolute joint mechanism, or that reports on a linear displacement for a linear joint provided by a prismatic joint mechanism. And, the sensor system 108 may include, or otherwise have access to, a clock for determining angular or linear changes over time to determine a velocity or a component of velocity (e.g. speed). (Velocity is used here to mean linear or angular velocity. Example components of velocity include direction and speed. As a specific example, angular speed may be measured in radians per second.) Alternatively, or in addition, velocity, acceleration and other higher order derivatives or position could be calculated from reports of position changes over time. Velocity could also be determined more directly, such as by the sensor system 108 including a velocity sensor. Velocity can also be determined by accumulating over time (such as by integration) acceleration determined from an accelerometer positioned on links moved by articulation of the joint mechanism. Conversely, the position may also be determined from accumulating acceleration or velocity measurements. The joint state can also be determined for more complex joint mechanisms. For example, the sensor system 108 may report positions for joints having rotations and translations in three-dimensional space, such as in three-axes Cartesian coordinate systems. The sensor system 108 can also report information on the positions of individual components of pose of multi-component joint mechanisms. In any case, the sensor system 108 herein is not limited to direct sensing of the joint state and associated variables, various proxies can be sensed and the joint state variable derived from that proxy value, such as velocity from position.

Teleoperated medical system 100 also includes a feedback system to provide feedback to the operator or personnel or systems. Specifically, the FIG. 1 example includes a display system 110 for displaying an image or representation of the medical work site (for example, a surgical site for a surgical procedure) generated by any one or combination of: one or more instruments 104 with imaging capabilities, and one or more sub-systems of sensor system 108. Display system 110 and input device 106 may be oriented so operator O can control medical instrument 104 and input device 106 with the perception of telepresence.

In some embodiments, a plurality of medical instrument 104 is used, and at least one of the medical instruments 104 has a visualization system capable of imaging the medical site or other medical instrument(s) 104 at the medical work site. For example, a medical instrument 104 with a visualization system may include a viewing scope assembly that captures a real-time image of the medical work site, and other medical instrument(s), within its field of view. The medical system 100 provides the captured image to operator O or other personnel through one or more displays, such as one or more displays of display system 110 or other displays communicatively coupled to medical system 100. The capture image may also be provided to other equipment for recording, image processing, and the like. The concurrent or real-time image may be, for example, a two or three-dimensional image captured by an endoscope positioned within the medical work site.

In some examples, teleoperated medical system 100 may configure multiple medical instruments 104 and controls of input device 106 such that the relative positions of the medical instruments 104 are similar to the relative positions of the eyes and hands of operator O. As a specific example, a first medical instrument 104 may comprise an image device to which other medical instruments are referenced. The other medical instruments may be controlled to have positions and orientations relative to the field of view of the image device that is similar to the positions and orientations of the hands of the operator O to the field of view (represented by the eyes) of the operator O.

Teleoperated medical system 100 may also include the control system 112. The control system 112 includes at least one memory and at least one computer processor (not shown) for effecting control among medical instrument 104, manipulator assembly 102, input device 106, sensor system 108, and display system 110. Control system 112 also includes programmed instructions (e.g., a non-transitory machine-readable medium storing the instructions) to implement some, or all, of the methods described in accordance with aspects disclosed herein, including instructions for providing information to display system 110.

While control system 112 is shown as a single block in the simplified schematic of FIG. 1, the control system 112 may include two or more data processing circuits with one portion of the processing optionally being performed on or adjacent to manipulator assembly 102, another portion of the processing being performed at input device 106, and/or the like. The processors of control system 112 may execute instructions comprising instructions corresponding to processes disclosed herein and described in more detail below. Any of a wide variety of centralized or distributed data processing architectures may be employed. Similarly, the programmed instructions may be implemented as a number of separate programs or subroutines, or they may be integrated into a number of other aspects of the teleoperational systems described herein. In one embodiment, control system 112 supports wireless communication protocols such as Bluetooth, IrDA, HomeRF, IEEE 802.11, DECT, and Wireless Telemetry.

In some embodiments, control system 112 may receive force and/or torque feedback from medical instrument 104. Responsive to the feedback, control system 112 may transmit signals to input device 106. In some examples, control system 112 may transmit signals instructing one or more actuators of manipulator assembly 102 to move medical instrument 104. In some embodiments, the one or more actuators and manipulator assembly 102 are provided as part of a cart positioned adjacent to patient P and operating table T; in some embodiments, the manipulator assembly 102 is physically coupled to the operating table T or to a floor, a ceiling, or a wall of the operating area.

As noted above, the manipulator assembly 102 and/or medical instrument 104 may be moved in different modes of operation. These modes are implemented or assisted by the control system 112. For example, in the first, external articulation facilitation mode, the control system 112 can operate the sensor system 108 to sense externally applied forces on the joints, on links physically coupled to the joints, and/or articulations of the joints, and then instruct the actuators of those or other joints of the manipulator assembly 102 to at least partially assist in those articulations within certain parameters. For example, the control system 112 can instruct brakes or motors to counteract gravitational forces on a joint (a.k.a. gravity compensation). In this manner, manipulator assembly 102 has reduced drop, or does not drop, due to gravitational forces on that joint when entering the first, external articulation facilitation mode. Also, the operator, when trying to externally articulate or otherwise move a part of the manipulator assembly 102 and/or medical instrument 104 horizontally to a new location, has reduced or no need to support the manipulator assembly 102 and/or medical instrument 104 against the forces of gravity. Similarly, the control system 112 in this mode can reduce the effects of inertia, friction, or braking forces so that the operator expends less effort (e.g. apply lower forces and moments, input less energy) in articulating or otherwise changing the configuration of part or all of the manipulator assembly 102 and/or medial instrument 104. Also, the control system 112 can instruct the actuators to cause one or more links to follow the externally applied forces and articulations to further aid in repositioning of the manipulator assembly 102 and/or medical instrument 104 via externally applied forces.

In a second, forward driven mode the control system 112 implements the instructions created by the user through various controls used to teleoperate the manipulator assembly 102. Thus, unlike the external articulation described above in conjunction with the first mode, the forward driven articulations of the manipulator assembly 102 in this second mode are communicated through the control system 112. Forward driven articulation here refers to an actuator driven movement of the manipulator assembly 102 in whole or in part, as opposed to movement of the manipulator assembly that directly results from externally applied forces. Forward driven articulation involves motion commands generated by an algorithmic mechanism coupled with a feedback controller that guides the actuator to follow the commands. Generally, the control system 112 in the second mode is configured to not facilitate external articulation the manipulator assembly 102 in response to forces applied externally to the manipulator assembly 102 and/or medical instrument 104. Also, it should be noted that the control system 112 can also be configured to operate in other modes, and in combinations or other mixtures of the external articulation facilitation and forward driven modes. For example, the control system 112 may be operated in a teleoperated mode. Teleoperation involves both forward-driving and user-input for commanding the forward-driving. Alternatively, the first mode could combine just forward-driving and automated motion commands. In the forward driven mode, the control system 112 imposes limits on the commands sent to the actuators resulting from movement of the input device 106, such that the commanded accelerations, velocities, or positions are limited in the command. And, the control system 112 is configured to progressively reduce, such as by providing a linear decrease that may be described as a chamfer (for a smooth reduction), these limits on the commanded accelerations, velocities, or positions as the manipulator assembly 102 reaches range of motion limits-such as mechanical limits constituting hard stops.

The term "mechanical limit" as used herein can include any physical feature that can interfere with the motion of the joint. For example, the opposite ends of the path of motion of a hinge joint mechanism define two mechanical limit locations. Mechanical limits are not limited to joint mechanisms between two links, but can also be expressed as combinations of joint mechanisms reaching a physical limitation dependent on the pose of a plurality of links of a manipulator assembly 102. Other joint mechanisms, such as other revolute, prismatic, or multi-degree-of-freedom joint mechanisms can also have mechanical limits and benefit from embodiments of the present invention.

Embodiments of the present invention are useful when aspects of the first mode—where the control system 112 is facilitating external articulation of joint mechanisms of the manipulator assembly 102 due to application of external forces—are being employed by the system 100 and there is some risk that the external articulation of the joint may impact or overload a mechanical limit of the joint mechanism implementing the joint. When facilitating external articulation, the externally applied load or kinetic energy is not commanded by the controller and excessive externally applied load or kinetic energy can impact or overload the mechanical limit of the joint mechanism. Embodiments of the present invention are particularly useful in manipulator assemblies where links or other components of the manipulator assembly have a mass large enough to generate a spike in loading when decelerating due to physical impact at a mechanical limit. Embodiments of the present invention mediate these events by resisting movement of the joint when it reaches certain position and movement criteria. For example, for a joint with a rotational degree of freedom, the control system 112 may be configured to apply a torque to the joint when the angular velocity of the joint exceeds a threshold in the direction of the mechanical limit location. The torque may be applied to provide a motion damping effect that dissipates the kinetic energy associated with the movement of the joint (including any components moved by motion of the joint mechanism). For example, the torque may be applied in proportion to the amount joint velocity exceeds the threshold for a viscous damping effect. Similarly, for a joint with a linear degree of freedom, control system 112 may be configured to apply a linear resistive force to the joint when the linear velocity of the joint exceeds a threshold dependent on the direction of motion of the joint relative to mechanical limit(s) of the joint, and such linear force may be applied to provide a damping effect.

Note that applying resistance against externally applied articulation of a joint in the external articulation facilitation mode is different than modifying the commands sent to the actuators to limit the commanded motion of the joint in the forward driven mode. In the teleoperated mode, the system can avoid commanding movement that impacts or overloads the joint mechanism's mechanical limit.

It should be noted that although some embodiments herein are described as using torque to resist rotation of a rotational joint, linear forces could also be applied to joints to resist external articulation in excess of velocity profiles. Combinations of linear forces and torques may also be applied, depending on the type of joint and the external articulation being resisted.

It should be noted that control systems 112 can have other limiters applied to externally applied articulations of the manipulator assembly. For instance, in the external articulation facilitation mode, the control system 112 may include a software-implemented stop that is reached before the joint reaches the mechanical limit location. The control system 112 can be configured to cause the actuators to oppose motion past the soft stop and push the joint back to the soft stop when the joint travels past the soft stop. Embodiments of the present invention can be applied along with or overlaid on these other limiting features for additional protection against movements near and over the range of motion of the manipulator assembly 102.

The terms "resist" and "resistance" as used herein in the context of a joint or its joint mechanism include any torque, friction, braking or other force (or combination of forces), or differential in forces, applied by an actuator associated with the joint and that impedes but does not fully prohibit external articulation of the joint during the first mode. Generally, in most circumstances, the resistance in the first mode is less than a resistance arising when the operator attempts to move the manipulator assembly 102 and it is not in the first mode, i.e., the control system 112 is not facilitating articulation due to external inputs. The resistance may also be expressed as a reduction in the facilitation of the articulation of the joint in response to the externally applied forces or articulations. A force may be a resistance force even if only a component of the overall force opposes the externally applied forces inducing articulation of the joint toward a mechanical limit location.

Figure 2:
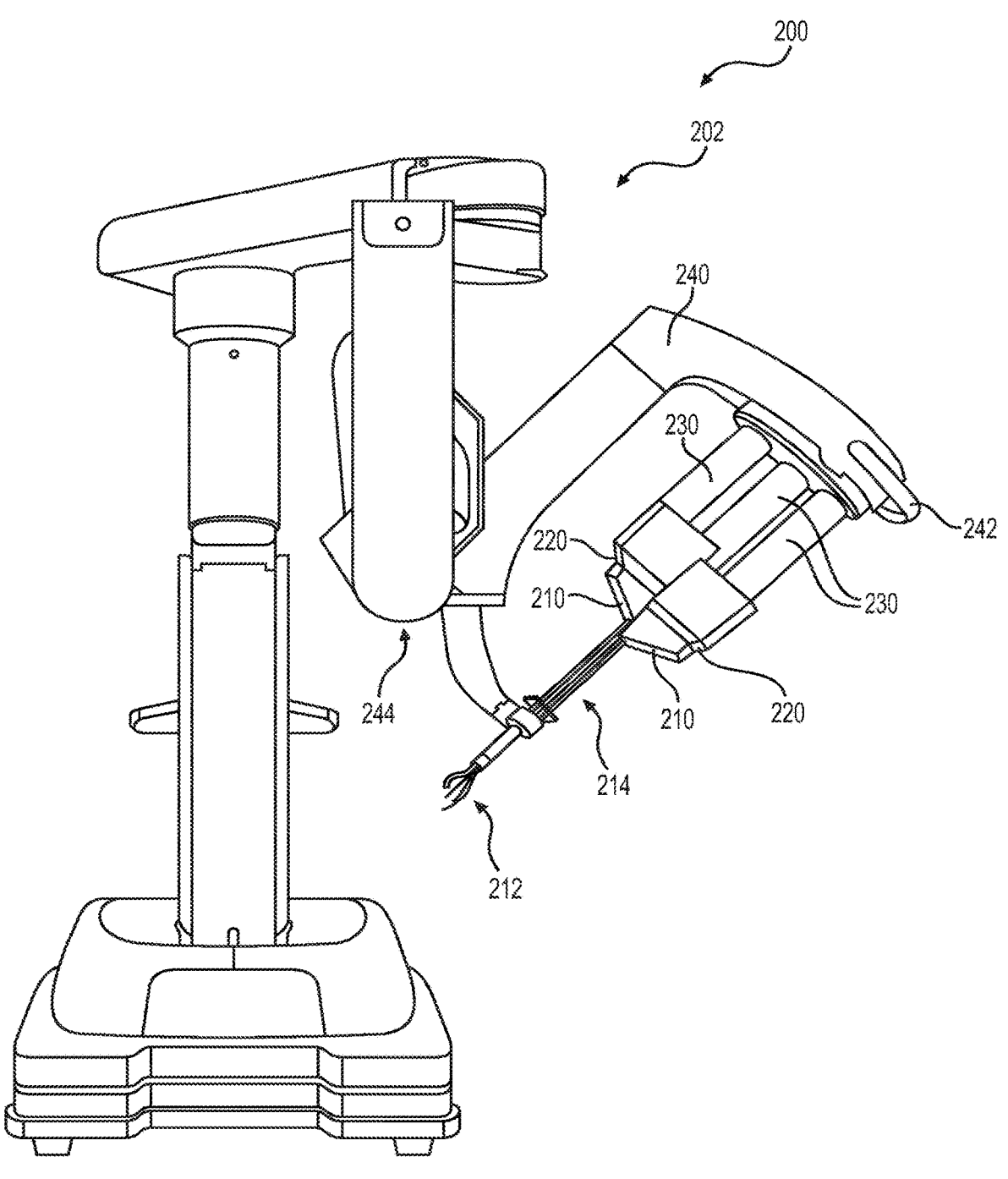
FIG. 2 shows an implementation of a medical system employing removable instruments of another embodiment of the present invention.

FIG. 2 shows an example of a medical system 200 including replaceable medical instruments 210 that includes links with mechanical limits and benefits from embodiments of the present invention. System 200, employs multiple instruments 210, each of which is mounted in an instrument mount 220 on a manipulator arm 230 of a manipulator assembly 202. A sterile barrier (not shown in FIG. 2) including a drape and instrument adaptors may be between a patient (not shown) and manipulator assembly 102. Manipulator assembly 202, including manipulator arms 230 and instrument mounts 220, may thus be outside a sterile environment for the patient, while instruments 210 are in the sterile environment on the patient's side of the sterile barrier. Accordingly, manipulator assembly 202 may not need to be sterilized for medical procedures.

Instruments 210 may vary in structure and purpose but may still be interchangeable, so that a user can select and mount various instruments 210 in instrument mounts 220 of manipulator assembly 202 as needed for a particular medical procedure and can change instruments 210 during a medical procedure to provide desired clinical functions. Each instrument 210 generally includes an end effector, sensor, or other distal tool 212, an instrument shaft 214, and an instrument backend configured to couple to the instrument mounts 220. Instrument mounts 220 of manipulator assembly 202 may include actuators such as drive motors, or transmission systems that transmit forces or torques from actuators, through the sterile barrier to the instruments 210 to provide mechanical power to actuate mechanical structures in instruments 210.

Distal tools 212 may have different designs to implement many different functions. For example, distal tools 212 for different instruments 210 may have many different functions, shapes, or sizes and may include graspers, knives, scissors, energy application tools such as ablation and cautery tools, needles, hooks, suction tips, irrigators, specimen retrieval bags, light emitters, or sensing devices such as optical or ultrasonic imagers, drivers to name a few possibilities. Instruments 210 having different distal tools 212 may be mounted on different arms 230 of manipulator assembly 202 and may work cooperatively at the same work site. An endoscopic camera, for example, a stereoscopic camera, can also be mounted on an arm to provide visual information, particularly images of the work site in which distal tools 212 of instruments 210 may be operating.

System 200 of FIG. 2 may be operated in a first mode, wherein an operator indicates to the control system 112 that operation in the first mode is to be commenced-such as by gripping a bar on a handle 242 or depressing a pedal. The control system 112 is then signaled to facilitate the manipulator arm 230's articulation in response to the externally applied forces. For example, the user can continue to push the handle 242 or push an instrument mount 220 to articulate the manipulator arm 230 or instruments 210 into desired positions or orientations, such as proximate a patient orifice or other patient anatomy during setup for a procedure. In this first mode, the control system 112 is selecting amongst various actuators to either reduce braking of the joints to reduce the energy needed for articulation of the joints, or to positively assist in the articulation of the joints or resist other forces on the joints, such as gravity. Actuators, such as servos under feedback control, for example, can be used to follow along with external forces and motions to reduce the slowing effects of the mass of the components of the system 200. Also, the control system 112 may use brakes to prevent the links and joints from moving unintentionally due to the forces of gravity. In another example, the control system 112 may just reduce braking by releasing one or more selected brakes partially or entirely, to facilitate rotations and translations in the first mode.

Notably, the system 200 of FIG. 2 is primarily configured for performing medical procedures through a single orifice resulting in clustering of the instrument shafts 214 and associated docking ports about a single axis extending collinear with the shafts. This configuration results in a relatively massive assembly that has a significant amount of mass cantilevered out from a plurality of joint mechanisms, such as joint mechanism 244. The joint mechanism 244 is a revolute joint mechanism that implements a rotational degree of freedom. Joint mechanism 244 supports all of the instruments 210 (when present), their instrument mounts 220, and heavy portions of the manipulator arm 230 longitudinally offset from the axis of the joint mechanism 244. The term "heavy" is used in the context of the relative size or mass of the other components of the system and indicates an increased likelihood of overloading mechanical limits because of such a relatively higher size or mass of a mechanical component contributing to the mechanical limits. Thus, when operating in the first mode, the control system 112 applies brakes and/or actuators to hold the joint of joint mechanism 244 at an angle against gravity while still moving to follow the externally applied forces of the operator. Due to the cantilevered mass of the relatively heavy single-port arm configuration, the operator may overload the mechanical limits by applying a heavy external force or fast articulation and run components of joint mechanism 244 into the mechanical limits at either end of the joint mechanism 244.

In some embodiments, the control system 112 is configured to command one or more actuators to resist articulation of the one or more joint mechanisms (such as the joint mechanism 244 of the system 200 of FIG. 2) of the manipulator assembly 202 when the manipulator assembly 202 has certain joint states and is (at least partially) operating in the first mode. For example, the control system 112 may include a memory storing a plurality of velocity criteria. A first velocity criterion, for example, can be associated with the joint being at a first position and moving toward the mechanical limit. A second velocity criterion can be associated with the joint being at a second position and moving toward the mechanical limit. The control system 112 is configured to command the actuator of the joint to resist articulation of the joint in response to the joint state indicating the joint is at the first joint position and is moving toward the mechanical limit with a joint velocity meeting the first joint criterion. The control system is also configured to command the actuator of the joint to resist movement of the joint in response to the joint state indicating the joint is at the second joint position and moving toward the mechanical limit with a joint velocity meeting the second joint criterion.

Figure 3:
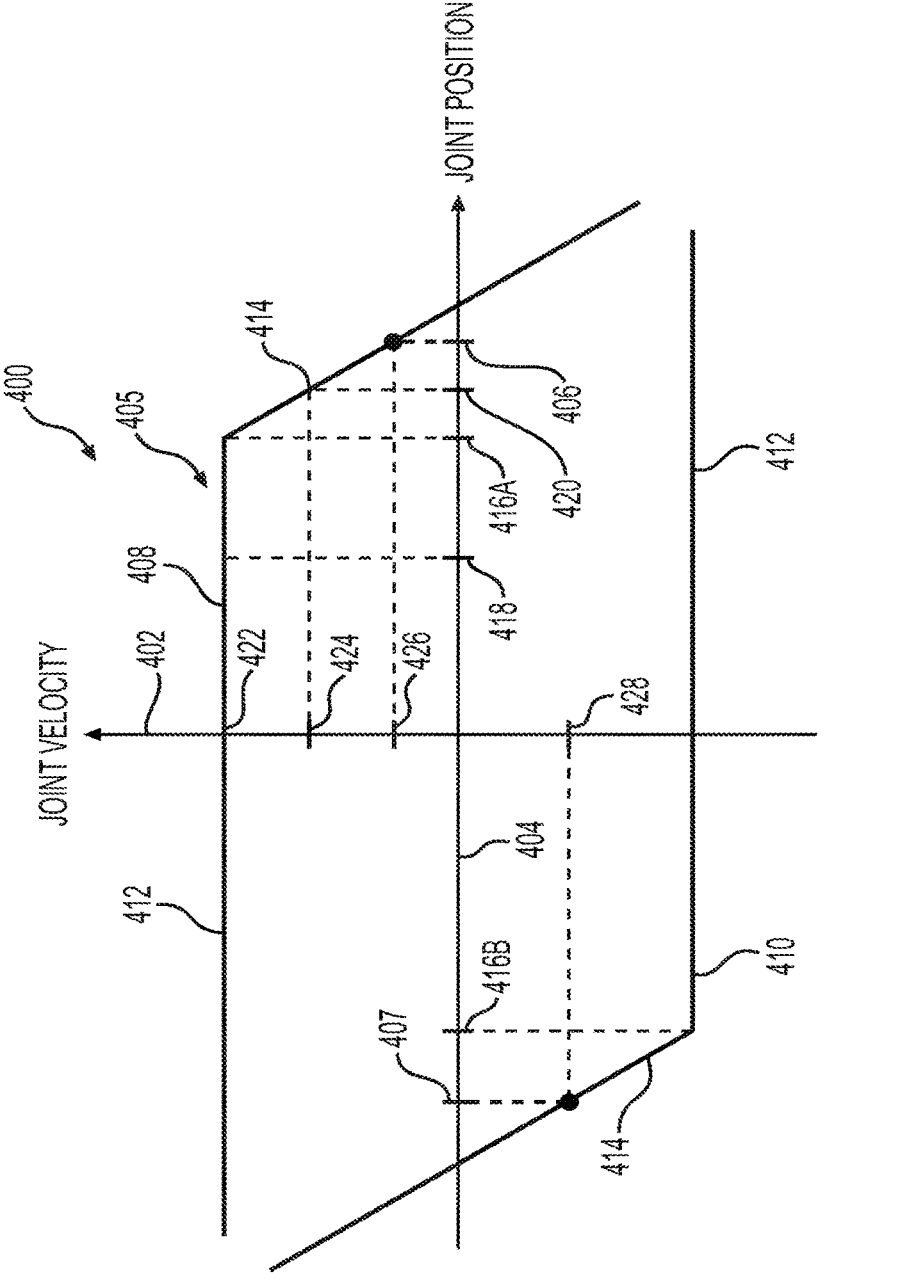
FIG. 3 shows a schematic of velocity threshold criteria corresponding to joint states of another embodiment of the present invention.

FIG. 3 depicts a graph 400 showing how, in one embodiment, the control system 112 may include or access a velocity and position profile stored in memory to address possible mechanical limit overload at the ends of the range motion of a single degree of freedom for a joint mechanism. Each velocity profile associates a plurality of velocity criteria with at least one joint position. Generally, the graph 400 includes a vertical axis 402 indicating joint velocity and a horizontal axis 404 indicating joint position. Along the horizontal axis are a first mechanical limit location 406 and a second mechanical limit location 407 that indicate first and second mechanical limit locations, respectively defined by first and second mechanical limits of the joint mechanism. The mechanical limit locations 406 and 407 bracket the extreme ranges of motion of the revolute joint mechanism along the joint position axis and correspond with the joint limits—such as an upper and lower joint position limit for the joint mechanism. Exceeding these positions in the positive or negative direction risks damaging the joint mechanism.

The graph 400 shows a velocity profile 405 having a positive velocity profile portion 408 and a negative velocity profile portion 410. The terms positive and negative are arbitrary and are used in "positive velocity profile portion 408" and "negative velocity profile portion 410" for convenience in indicating direction of motion relative to the mechanical limit associated with mechanical limit location 406. That is, "positive velocity profile portion 408" is used herein to indicate velocity with a direction of motion toward the mechanical limit associated with the first mechanical limit location 406, and "negative velocity profile portion 410" is used herein to indicate velocity with a direction of motion away from the mechanical limit associated with the first mechanical limit location 406 (even though the velocity would then move toward the mechanical limit associated with the mechanical limit location 407. Thus, the actual values and calculations used to indicate "positive velocity"

or "negative velocity" in various implementations can be positive or negative or unsigned, depending on factors such as how mechanical limit locations, or how directions of motion are referenced or stored. The positive velocity profile portion 408 applies only to motions in the direction toward the first mechanical limit location 406 while the negative velocity profile portion 410 applies only to motions in the direction away from the first mechanical limit location 406 and toward the second mechanical limit location 407. It should also be noted that the control system may have and apply other limits, as mentioned above, such as an overall velocity limit that is not dependent on the position or direction of the movement of the joint mechanism. Such other limits may be applied in combination to augment the limits described above, in a linear or nonlinear manner.

Returning to FIG. 3, the two profile portions 408, 410 are symmetric about a diagonal and therefore have matching velocity limits at positions relative to the mechanical limits which, when exceeded, result in the control system 112 instructing an actuator to apply a resistance. Each of the profile portions 408, 410 includes a constant velocity threshold 412 and a decreasing velocity threshold 414. The constant velocity threshold 412 remains in a straight horizontal line and is thus constant for all positions from the opposite mechanical limit up to a transitional position 416A or 416B. The decreasing velocity threshold 414 is a straight line on a diagonal extending from the transitional position 416A or 416B in the direction of the respective adjacent mechanical limit location 406 or 407. Thus, when the joint moves within the transitional position 416A or 416B the threshold velocity decreases linearly with the decreasing distance from the adjacent mechanical limit location 406 or 407.

Notably, the decreasing velocity threshold 414 does not intersect the mechanical limit location 406 along the horizontal axis 404. In the embodiment of FIG. 3, therefore, the control system 112 is configured not to apply any resistance to the joint for joint speeds below a certain minimum velocity criterion that is above zero. This allows the operator to move the joint to the mechanical limit at or below a first minimum speed threshold 426 without a reduction in or opposition to the facilitation that occurs in the first mode. The same applies for the decreasing velocity threshold 414 of the negative velocity profile portion 410 such that articulations below a second minimum speed threshold 428 are not subject to resistance even in the direction of the mechanical limit associated with mechanical limit location 407. (As noted elsewhere, however, other limitation schemes may cause control system 112 to react to resist joint positions close to mechanical limits according to other criteria.)

The illustrated profile portions 408, 410 are one representation of a plurality of velocity criteria that are associated with a joint state. Although the illustrated velocity profile portions 408, 410 are linear and symmetric, other embodiments may have non-symmetric velocity profiles or only a single velocity profile-protecting only one mechanical limit. Multiple velocity profiles may also be maintained for the same mechanical limit or for each of multiple (such as three or more) mechanical limits in more complex systems. And, the velocity criteria may be expressed as collections of data points, equations or other curves or shapes, or combinations thereof, that relate the joint state to threshold velocities at which the control system 112 is configured to apply resistance to the joint. For example, the velocity profile may be determined by a curve wherein threshold velocity drops off more steeply than the distance decreases toward the mechanical limit. Thus, the velocity criteria need not be a collection of values stored in a memory and associated with corresponding joint states.

Figures 4A, 4B, 4C:
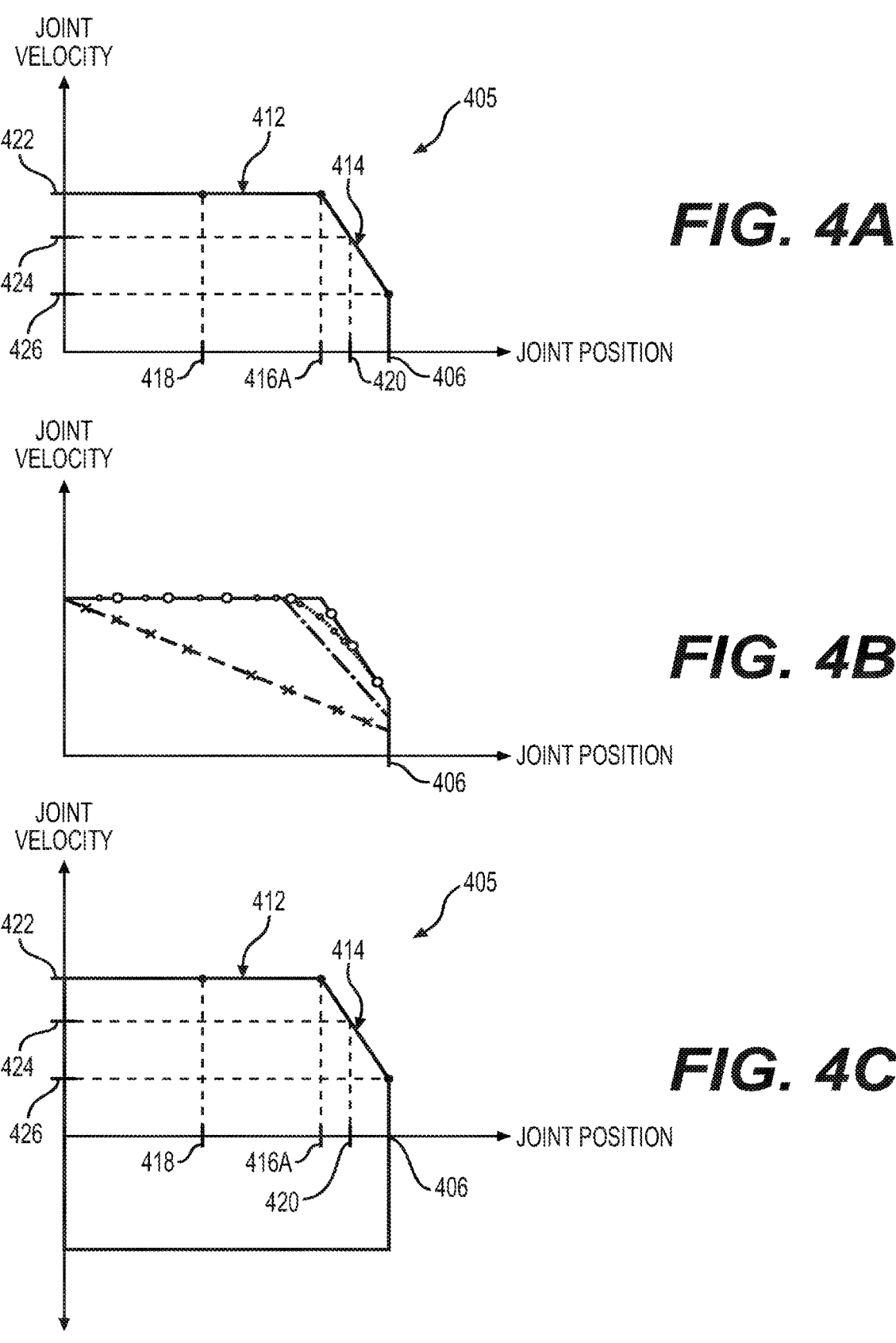
FIG. 4A-4D show schematics of velocity threshold criteria of other embodiments of the present invention.

FIGS. 4A-4D illustrate other embodiments of velocity and position profiles that may be used by the control system 112. FIG. 4A, for example, shows a velocity profile 405 that is similar to the positive velocity profile portion of FIG. 3. The profile includes the constant velocity threshold 412 and the decreasing velocity threshold 414. The transitional position 416A is the transition between the constant velocity threshold 414 and the constant velocity threshold 412. If the sensor system 108 detects a velocity of the joint exceeding the first speed threshold 422, the actuator applies a resistance. If the sensor system 108 detects the joint location within a tolerance of the transitional position 416A, it calculates, for example, second speed threshold 424 from the decreasing velocity threshold 414. If the velocity of the joint exceeds the second speed threshold 424, the actuator applies a resistance. The decreasing velocity threshold 414 is a straight line that intersects the mechanical limit location 406 above zero and thus the actuator does not apply a resistance under the first minimum speed threshold 426.

FIG. 4B illustrates multiple exemplary velocity profiles 405 with different joint velocity threshold to joint position relationships, including velocity profiles 405 with no constant velocity sections, with nonlinear sections, different transition positions, and different slops of velocity threshold decrease relative to joint position.

FIG. 4C illustrates a velocity profile combining the velocity profile 405 of FIG. 4A for movement of the joint toward to mechanical limit location 406 (above zero on the vertical velocity axis) with a negative velocity threshold 413 for movement of the joint away from the mechanical limit location 406 (below zero on the vertical velocity axis). The negative velocity threshold 413, for example, is illustrated as a constant speed threshold 425 that is greater in magnitude than any of the first and second speed thresholds 422 and 424. Movements away from the mechanical limit location 406 may also be expressed by a range of profile shapes, such as those illustrated for movements toward the mechanical limit location.

Returning to FIG. 3, a first joint position 418 and a second joint position 420 provide an example of how the velocity criteria are defined by the positive velocity profile portion 408. The control system 112 determines that the joint is at a first joint position 418 and moving toward the direction of the mechanical limit location 406 (a first joint state). The control system 112 determines from the constant velocity threshold 412 that a first speed threshold 422 is a fixed velocity at the first joint state. If the sensor system 108 detects a velocity of the joint exceeding the first speed threshold 422, the actuator applies a resistance. For example, the control system 112 may subtract the first speed threshold 422 from the actual speed of the joint (reported by the sensor system 108) and instructs the actuator to apply a resistance in proportion to the magnitude of the velocity difference, mimicking a damped system.

The controller may command application of other resistance loads including forces for linear degrees-of-freedom and torques for rotational degrees-of-freedom. For example, the resistance load can be different functions of magnitude of the velocity difference mentioned above. This function may be a constant, $$g(v) = -g_0 * \text{sign}(v), , \qquad \text{equation 1}$$

$$g(v) = -b * v, , \qquad \text{equation 2}$$

$$g(v) = (\Sigma_0^n a_n * |v|^n) * -\text{sign}(v), , \qquad \text{equation 3}$$

where, v is the velocity difference mentioned above, $-g_0$ is a coefficient of friction, b is a coefficient of viscous resistance or linear drag coefficient, and $a_n$ is a polynomial constant. As shown above, equation 1 is a coulomb friction resistance load, equation 2 is a linear viscous resistance load, and equation 3 is a polynomial resistance load. Other resistance load functions may be used. Note that g(0), i.e. the resistance just at the velocity threshold, does not have to be 0. Resistance loads also may be a function of additional variables and also need not be a function of the velocity difference at all.

The control system can also detect the joint at the second joint position 420 and moving in the direction toward the mechanical limit location 406 (a second joint state). In this case, the control system 112 can determine a reduced second speed threshold 424 based on the velocity profile (e.g., the stored relationships, collection of points, or equation) and the decreasing velocity threshold 414 and the second joint state. The control system 112 may also calculate a magnitude of the resistance based on the magnitude of the difference between the actual joint speed and the second speed threshold 424.

Various embodiments may also include configuring the control system 112 to apply different resistance criteria. For example, the amount of resistance can be a constant resistance regardless of how much the velocity threshold is exceeded. Or, the control system 112 can be configured to more heavily weight the resistance—more than just linearly—with increasingly exceeded threshold velocities. More resistance could also be applied closer to the mechanical limit itself as the risk of an impact increases. Different resistances can be applied to differently sized joint mechanisms, based on expected kinetic energy for the associated joint articulation. The above-described resistance loads can also be applied to other velocity profiles such as, for example, to the embodiments of FIGS. 4A-4D.

For joint states reported by the sensor system 108 as having a velocity in the direction of the opposite mechanical limit (corresponding with mechanical limit mark 407), the positive velocity profile portion 408 does not apply. Instead, some other velocity profile may apply, such as a global velocity threshold. Even at the same first joint position 418, the global velocity threshold may yield a third velocity criterion having a threshold speed higher than the first speed threshold 422. Or, for embodiments corresponding with the symmetrical curves of FIG. 3 and having two mechanical limits in a joint mechanism, the negative velocity profile portion 410 applies with the same thresholds in the direction of the mechanical limit represented by the mechanical limit mark 407. In another instance, the control system 112 may apply no resistance in response to movement away from a mechanical limit at any position. For example, the control system 112 may, for one or more joint states with movement away from the mechanical limit, not command the actuator to resist movement of the joint. (As noted elsewhere, however, other limitation schemes may cause control system 112 to react to resist joint positions close to mechanical limits according to other criteria.)

In the graph 400 shown in FIG. 3, upon the joint position extending outside the range of motion defined by the mechanical limit locations 406, 407, a joint mechanism may apply a force in a direction of motion towards the range of motion in a restoring behavior. For example, an actuator motor may apply a torque to the joint in a direction of the range of motion. The restoring behavior may be considered an autonomous or non-passive motion of the joint. In the positive velocity profile 408, upon the joint position extending beyond the mechanical limit location 406 by a predetermined distance, the decreasing velocity threshold 414 changes sign such that the joint mechanism drives the joint with a negative velocity to restore the joint to a location within the range of motion. Likewise, in the negative velocity profile 410, upon the joint position extending beyond the mechanical limit location 407 by a predetermined distance, the decreasing velocity threshold 414 changes sign such that the joint mechanism drives the joint with a positive velocity to restore the joint to a location within the range of motion.

Figure 4D:
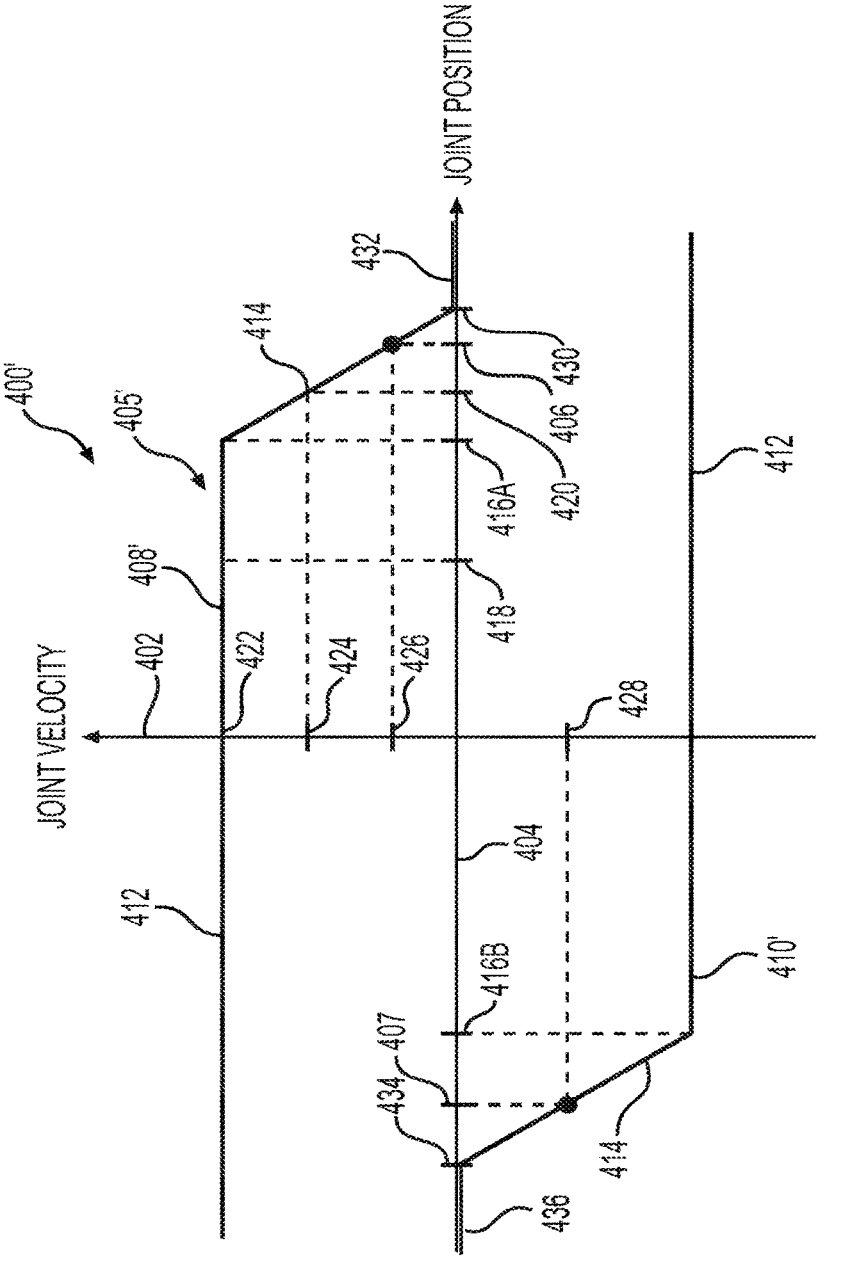

FIG. 4D depicts a graph 400' that shows a velocity profile 405' having a positive velocity profile portion 408' and a negative velocity profile portion 410'. The graph 400' is substantially similar to graph 400 described herein with reference to FIG. 3, with like numerals representing like parts. In contrast to the restoring behavior show in FIG. 3, the velocity profile 405' provides a passive behavior for motion of the joint outside the range of motion defined by the mechanical limit locations 406, 407. Therefore, the velocity profile 405' ensures that the positive velocity profile 408' does not have negative values and the negative velocity profile 410' does not have positive values. While a joint mechanism may not apply a force in a direction of motion towards the range of motion when the joint is outside of the range of motion, a joint mechanism may apply resistance if the sensor system 108 detects a velocity of the joint exceeding the velocity profile 408', 410'.

In the example shown in FIG. 4D, at a third joint position 430, the positive velocity profile 408' has a zero velocity threshold 432. Therefore, upon the joint reaching the third joint position 430, the joint mechanism provides a passive behavior for motion of the joint outside the range of motion. At a fourth joint position 434, the negative velocity profile 410' has a zero velocity threshold 436. Therefore, upon the joint reaching the fourth joint position 434, the joint mechanism provides a passive behavior for motion of the joint outside the range of motion. While the third and fourth joint positions 430, 434 are shown at a predetermined distance beyond the mechanical limit locations 406, 407, other positions may be used. For example, the third and fourth joint positions 430, 434 may be at the same position as the mechanical limit locations 406, 407. As another example, a magnitude of the distance beyond the mechanical limit locations 406, 407 may be different for the third and fourth joint positions 430, 434, respectively.

Figure 5A:
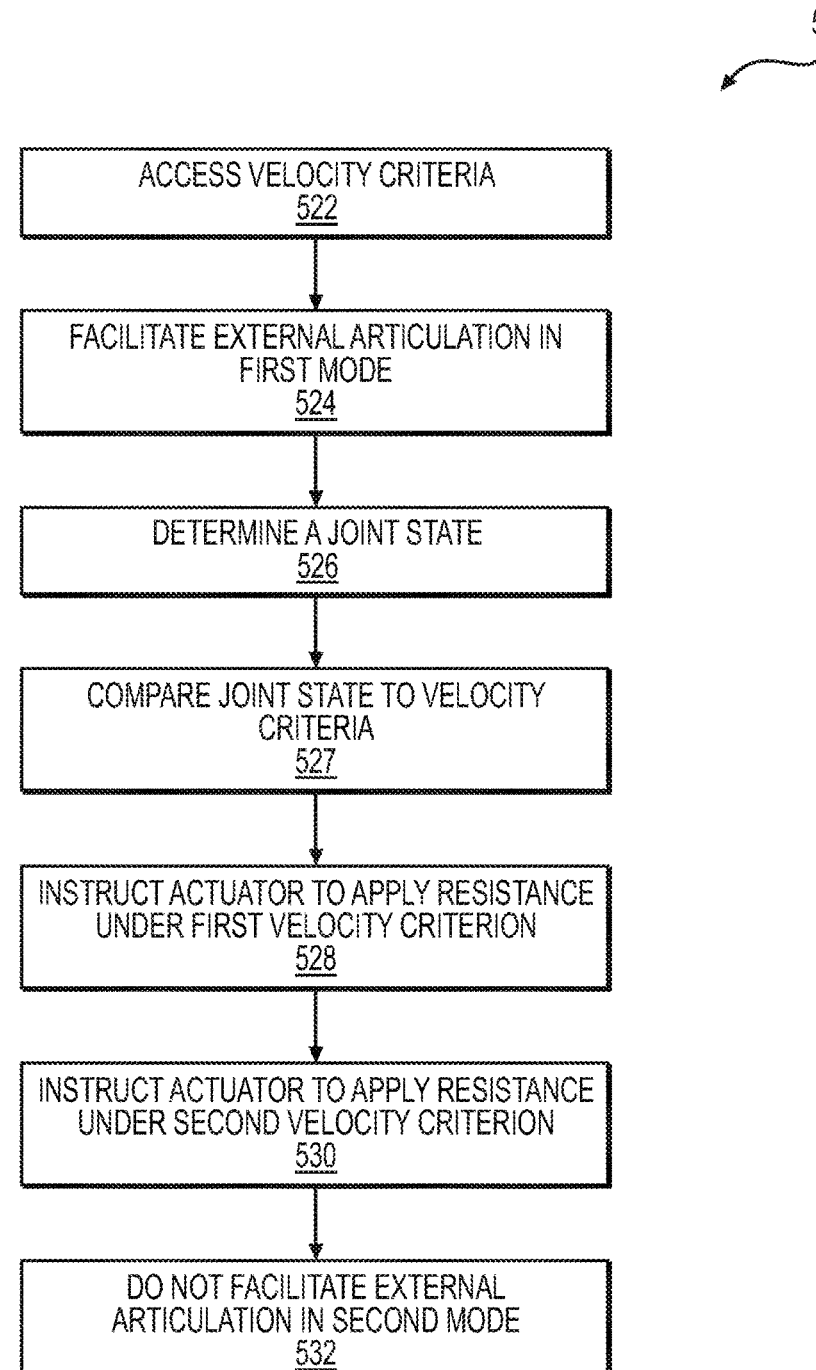
FIG. 5A shows a method of operating an articulable system of another embodiment of the present invention.

As shown in FIG. 5A, another embodiment can include a method of operating an articulable system (method 520). The articulable system includes a joint mechanism implementing a joint, an actuator physically coupled to the joint mechanism, a sensor system associated with the joint mechanism, and a controller, such as those described elsewhere herein. The joint mechanism includes a mechanical limit defining a mechanical limit location.

The method 520 includes accessing, with the controller, a plurality of velocity criteria (step 522). A first velocity criterion of the plurality of velocity criteria is associated with the joint being at a first joint position and moving toward the mechanical limit location. A second velocity criterion is associated with the joint being at a second joint position and moving toward the mechanical limit location. The method 520 further includes, while the articulable system is operating in a first mode, operating the actuator to facilitate external articulation of the joint (step 524). Also, while operating in the first mode, the method 520 includes determining a joint state (step 526), comparing the joint state to the velocity criteria (step 527), commanding the actuator to resist movement under the first velocity criterion (step 528) and commanding the actuator to resist movement under the second velocity criterion (step 530). The method also includes operating the actuator not to facilitate external articulation of the joint (step 532) when the articulable system is operating in a second mode.

Step 526, for example, includes determining a joint state using information from the sensor system, wherein the joint state comprises a joint position and a joint velocity. Step 528 can include commanding the actuator to resist movement of the joint in response to the joint state indicating the joint at the first joint position and moving toward the mechanical limit location with a joint velocity meeting the first velocity criterion. Step 530 can include commanding the actuator to resist movement of the joint in response to the joint state indicating the joint at the second joint position and moving toward the mechanical limit location with a joint velocity meeting the second velocity criterion.

Figure 5B:
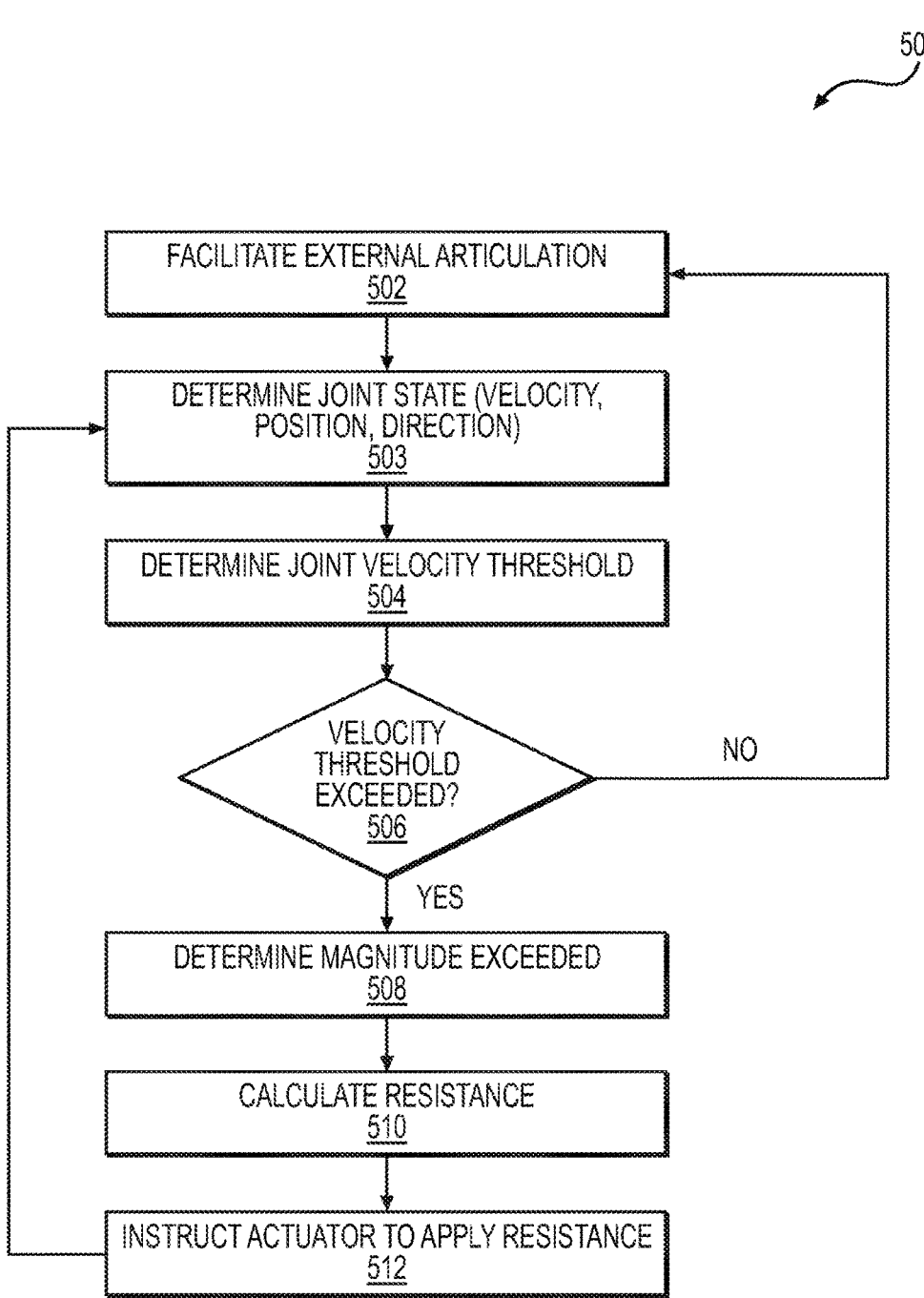
FIG. 5B shows a method of resisting externally applied articulations to a joint mechanism of another embodiment of the present invention.

As shown in FIG. 5B, another embodiment can include a method of protecting a mechanical limit (method 500). The control system 112, for example, may enter into the first mode wherein the control system begins to facilitate external articulation (step 502). For example, the control system 112 may detect an operator gripping a handle (such as handle 242), depressing of a foot pedal, or application of some external force to the manipulator assembly 102. The control system 112 in this mode selectively instructs various actuators to enable or case the motions applied by the operator and/or resists gravity and other frictional forces.

As articulation occurs, the control system 112 can monitor the states of the joint, such as by communicating with the sensor system 108 to determine the joint state (step 503). For example, the control system 112 can obtain data on a speed, position and direction of the joint mechanism-including whether that joint is heading toward a mechanical limit location. Next, the control system 112 can obtain or consult its own memory for a velocity profile associated with the joint states, such as the velocity profile shown graphically in FIG. 3. The control system 112 can use the determined joint state to then determine a joint velocity threshold (step 504), such as by calculating the threshold with an algorithm or comparing the joint state to a table or other database relating joint states to joint velocity thresholds.

Next, the control system 112 can compare the actual velocity of the joint from step 503 to the velocity threshold from step 504 to determine if the velocity threshold was exceeded (step 506). If the velocity threshold was not exceeded (No), the control system 112 continues to facilitate external articulation (step 502) with no resistance. If, however, the control system 112 determines the velocity threshold has been exceeded, it can calculate the magnitude 508 of the difference between the actual velocity and the velocity threshold. Then, the control system 112 can calculate a resistance (step 510), such as by multiplying a constant (resistance unit/speed) times the calculated magnitude 508. Then, the control system 112 can instruct the actuator to apply the calculated resistance from step 510.

Embodiments of the present invention can provide many advantages. For example, the systems and methods disclosed herein can help to protect against overriding a mechanical limit, especially in a manipulator assembly employing high mass links. In addition, because the system generates a resistance, it can be used for externally (outside of the controllers) applied articulations when restricting articulation commands from the control system may not arrive in time or be proportioned enough to avoid impacts. Also, the systems and methods allow for increased amounts of dissipation of kinetic energy sooner when a joint is closer to its mechanical limits. At the same time, the systems and methods can allow for un-resisted movement in the proximity of the mechanical limits below a certain threshold. Further, embodiments may be used in conjunction with other protective control schemes, including those in modes where external articulations are being applied to the joint.

The invention claimed is:

1. An articulable system comprising:
   a joint mechanism comprising a joint and having a mechanical limit, the mechanical limit defining a mechanical limit location;
   an actuator physically coupled to the joint mechanism;
   a sensor system associated with the joint mechanism and configured to sense a joint state of the joint, the joint state including at least one of a speed, a position, or a direction of movement of the joint; and
   a controller in communication with the sensor system and the actuator, the controller configured to, when in a mode in which the actuator at least partially assists movement of the joint due to a first externally applied force:
      determine a joint velocity threshold based on the joint state and a velocity profile, wherein the velocity profile defines a plurality of velocity criteria each associated with at least one joint position of the joint and relative to the mechanical limit location; and
      command the actuator to resist movement of the joint due to a second externally applied force in response to determining that: (i) the joint velocity threshold is exceeded, and (ii) the joint is moving toward the mechanical limit location.

2. The articulable system of claim 1, wherein the plurality of velocity criteria include a first velocity criterion associated with the joint being at a first joint position and moving toward the mechanical limit location and a second velocity criterion associated with the joint being at a second joint position and moving toward the mechanical limit location.

3. The articulable system of claim 2, wherein:
   the first joint position is farther from the mechanical limit location than the second joint position; and
   the first velocity criterion comprises a first speed threshold and the second velocity criterion comprises a second speed threshold lower than the first speed threshold.

4. The articulable system of claim 2, wherein the velocity profile comprises one selected from a group consisting of:
   a constant velocity criteria portion, the first velocity criterion being within the constant velocity criteria portion, and
   a decreasing velocity criteria portion, the second velocity criterion being within the decreasing velocity criteria portion.

5. The articulable system of claim 2, wherein the plurality of velocity criteria include a minimum velocity criterion associated with the joint being at the mechanical limit location, and wherein the minimum velocity criterion comprises a speed threshold greater than zero.

6. The articulable system of claim 1, wherein the controller is further configured to:

facilitate articulation of the joint due to the first externally applied force if the joint velocity threshold is not exceeded by allowing movement of the actuator without resistance.

7. The articulable system of claim 1, wherein the controller is further configured to:

determine a resistive force to be applied by the actuator based on a difference between the joint state and the joint velocity threshold.

8. The articulable system of claim 7, wherein to determine the resistive force includes to:

determine a magnitude of the difference between a measured velocity of the joint and the joint velocity threshold, the measured velocity of the joint determined from the joint state; and multiply the magnitude of the difference by a predetermined value.

9. The articulable system of claim 1, wherein the articulable system is a robotic system comprising a manipulator arm, wherein the manipulator arm comprises the actuator, the sensor system, and a kinematic series comprising the joint mechanism.

10. The articulable system of claim 1, wherein the mechanical limit is a first mechanical limit and wherein the joint mechanism includes a second mechanical limit defining a second mechanical limit location, wherein the controller is further configured to command the actuator to resist movement of the joint due to a third externally applied force in response to determining that: (i) the joint velocity threshold is exceeded, and (ii) the joint is moving toward the second mechanical limit location.

11. The articulable system of claim 1, wherein the controller is further configured to:

detect actuation of the joint mechanism due to the first externally applied force, wherein the joint state of the joint is monitored responsive to detecting actuation.

12. A method of operating an articulable system comprising: (i) a joint mechanism comprising a joint and a mechanical limit defining a mechanical limit location, (ii) an actuator physically coupled to the joint mechanism, (iii) a sensor system associated with the joint mechanism and configured to sense a joint state, and (iv) a controller, the method comprising:

determining, by the controller, when in a mode in which the actuator at least partially assists movement of the joint due to a first externally applied force: a joint velocity threshold based on the joint state and a velocity profile, wherein the velocity profile defines a plurality of velocity criteria each associated with at least one joint position of the joint and relative to the mechanical limit location; and commanding, by the controller, the actuator to resist movement of the joint due to a second externally applied force in response to determining that: (i) the joint velocity threshold is exceeded, and (ii) the joint is moving toward the mechanical limit location.

13. The method of claim 12, wherein the plurality of velocity criteria include a first velocity criterion associated with the joint being at a first joint position and moving toward the mechanical limit location and a second velocity criterion associated with the joint being at a second joint position and moving toward the mechanical limit location.

14. The method of claim 13, wherein:

the first joint position is farther from the mechanical limit location than the second joint position; and the first velocity criterion comprises a first speed threshold and the second velocity criterion comprises a second speed threshold lower than the first speed threshold.

15. The method of claim 13, wherein the velocity profile comprises one selected from a group consisting of:

a constant velocity criteria portion, the first velocity criterion being within the constant velocity criteria portion, and a decreasing velocity criteria portion, the second velocity criterion being within the decreasing velocity criteria portion.

16. The method of claim 13, wherein the plurality of velocity criteria include a minimum velocity criterion associated with the joint being at the mechanical limit location, and wherein the minimum velocity criterion comprises a speed threshold greater than zero.

17. The method of claim 12, further comprising:

facilitating articulation of the joint due to the first externally applied force if the joint velocity threshold is not exceeded by allowing, by the controller, movement of the actuator without resistance.

18. The method of claim 12, further comprising:

determining, by the controller, a resistive force to be applied by the actuator based on a difference between the joint state and the joint velocity threshold.

19. The method of claim 18, wherein the resistive force is determined by:

determining a magnitude of the difference between a measured velocity of the joint and the joint velocity threshold, the measured velocity of the joint determined from the joint state; and multiplying the magnitude of the difference by a predetermined value.

20. The method of claim 12, wherein the mechanical limit is a first mechanical limit and wherein the joint mechanism includes a second mechanical limit defining a second mechanical limit location, the method further comprising:

commanding, by the controller, the actuator to resist movement of the joint due to a third externally applied force in response to determining that: (i) the joint velocity threshold is exceeded, and (ii) the joint is moving toward the second mechanical limit location.

* * * * *